United States Patent

Kim et al.

[11] Patent Number: 5,138,088
[45] Date of Patent: Aug. 11, 1992

[54] NITROBENZOYL-3-CYCLO-PROPYLAMINOACRYLATES AND A PROCESS FOR THE PREPARATION THEREOF

[75] Inventors: You Seung Kim; Sang Woo Park; Jea Cheol Kim, all of Seoul, Rep. of Korea

[73] Assignee: Korea Advanced Institute of Science and Technology, Seoul, Rep. of Korea

[21] Appl. No.: 522,174

[22] Filed: May 10, 1990

Related U.S. Application Data

[62] Division of Ser. No. 321,971, Mar. 10, 1989, Pat. No. 4,965,396.

[30] Foreign Application Priority Data

Jun. 17, 1988 [KR] Rep. of Korea ................ 7381/1988

[51] Int. Cl.$^5$ ........................................... C07C 205/06
[52] U.S. Cl. ...................................... 560/21; 560/22; 560/23; 560/43
[58] Field of Search ...................... 560/21, 22, 23, 43

[56] References Cited

U.S. PATENT DOCUMENTS

| | | | |
|---|---|---|---|
| 4,695,646 | 9/1987 | Maurer et al. | 560/43 |
| 4,699,992 | 10/1987 | Grohe | 560/21 |
| 4,711,898 | 12/1987 | Enomoto et al. | 560/43 |

Primary Examiner—Jose G. Dees
Assistant Examiner—Porfirio Nazario
Attorney, Agent, or Firm—Darby & Darby

[57] ABSTRACT

Nitrobenzoyl-3-cyclopropylaminoacrylates are prepared by two stage reaction: a) The first stage is the synthesis of nitrobenzoyl-3-alkoxyacrylates from nitrobenzoylester compound and alkylorthoformate in organic acid solvent. b) The second stage is the synthesis of nitrobenzoyl-3-cyclo propylamino acrylate from nitrobenzoyl-3-alkoxyacrylates and cyclopropylamine.

4 Claims, No Drawings

NITROBENZOYL-3-CYCLOPROPYLAMINOA-CRYLATES AND A PROCESS FOR THE PREPARATION THEREOF

This is a division of application Ser. No. 321,971, filed Mar. 10, 1989, now U.S. Pat. No. 4,965,396.

BACKGROUND OF THE INVENTION

The present invention relates to nitrobenzoyl-3-cyclopropylaminoacrylates of the formula (I) and the preparation process thereof.

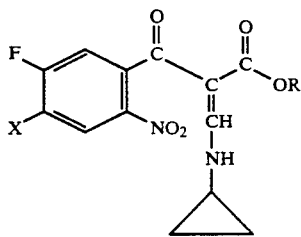

(I)

wherein
R = methyl, ethyl or propyl
X = halogen (chloro, fluoro or bromo)

Nitrobenzoyl-3-cyclopropylaminoacrylates of the formula (I) are the good intermediate for the preparation of quinolon derivatives (IV) with strong sterilization effect for bacteria (antibacterial agent).

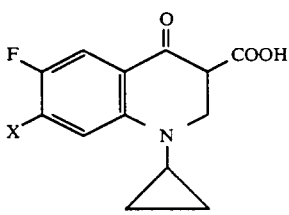

(IV)

wherein
X = halogen (chloro, fluoro or bromo)

The process for the preparation of nitrobenzoyl-3-cyclopropylaminoacrylates of the formula (I) consists of two stage reactions:

The first stage is to prepar nitrobenzoyl-3-alkoxyacrylates of the formula (III), which can be obtained by reacting nitrobenzoylester compound of the formula (II) with alkylorthoformate in organic acid solvent and the second one is to prepare nitrobenzoyl-3-cyclopropylaminoacrylates of the formula (I), which can be obtained by reacting nitrobenzoyl-3-alkoxyacrylates of the formula (III) and cyclopropylamine.

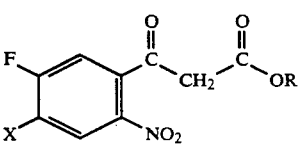

(II)

wherein
R = methyl, ethyl or propyl
X = halogen (chloro, bromo or fluoro)

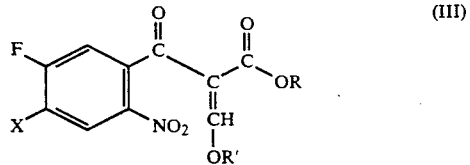

(III)

wherein
R = methyl, ethyl or propyl
X = halogen (chloro, fluoro or bromo)

DETAILED DESCRIPTION OF THE INVENTION

The detailed preparation method of nitrobenzoylester compounds of the formula (II) from dihalobenzene is described in the previous patent application Ser. No. 321,972 of the same inventors and assignee filed Mar. 10, 1989 on "Benzoylacetic Ester Derivatives and a Process for the Preparation Thereof", claiming priority from Korean application No. 7342/1988, filed Jun. 17, 1988.

Briefly, the benzoyl ester derivatives of formula II are prepared by reacting 5-fluoro-4-halo-2-nitrobenzoic acid with a chlorinating agent, such as thionyl chloride or trichlorophosphorous, followed by reacting the acid chloride so formed with a dialkylmalonate. The 4,5-difluoro-2-nitrobenzoic acid starting material can be prepared by nitration in mixed acid of 3,4-difluorobenzoic acid, which is obtained by oxidation 3,4-difluoroacetophenone. The 4- chloro-5-fluoro-2-nitrobenzoic acid starting material can be obtained by the following process:

(1) 3,4-dichloroacetophenon is nitrated to form 4,5-dichloro-2-nitroacetophenon.

(2) 4,5-dichloro-2-nitroacetophenon is then reacted with metal fluoride in a polar solvent to form 4-chloro-5-fluoro-2-nitroacetophenon.

(3) 4-chloro-5-fluoro-2-nitroacetophenon is oxidized by treatment with a chromic acid solution or a bromine/sodium hydroxide solution to obtain 4-chloro-5-fluoro-2-nitronitrobenzoic acid.

The nitrobenzoyl-3-alkoxyacrylates of the formula (III) can be obtained by refluxing the acetic acid anhydrous solution of nitrobenzoyl ester compound of the formula (II) and ethyl or methylorthoformate for 1 to 5 hours.

Wherein the equivalent ratio between alkylorthoformate and nitrobenzoylester compound of the formula (II) is preferably from 1.2 to 1.5.

Nitrobenzoyl-3-cyclopropylaminoacrylates of the formula (I) are prepared by adding cyclopropylamine to nitrobenzoyl-3-alkoxyacrylates of the formula (III), then stirring 18°-30° C. for 1 hour wherein the equivalent ratio between cyclopropylamine and nitrobenzoyl-3-alkoxyacrylate is preferably from 1.2 to 1.5.

In order to describe this invention more precisely, we have an example as follows;

This example is the synthetic process of nitrobenzoyl-3-cyclopropylaminoacrylate of the formula (I) from the compound of the formula (II).

In this case, R = ethyl and X = chloro in formula (II), R' = methyl in formula (III) and R = ethyl and X = chloro in formula (I) are confined.

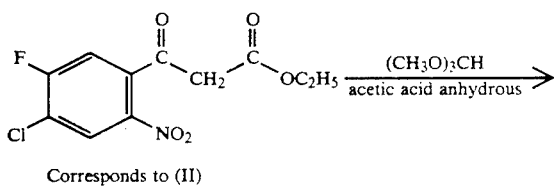

Corresponds to (II)

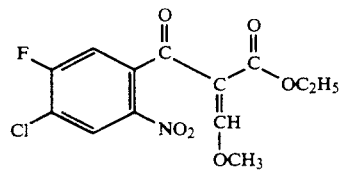

Corresponds to (III)

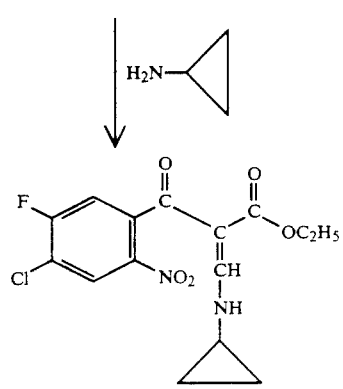

Corresponds to (I)

The present invention will now be described in detail with reference to the following examples.

EXAMPLE 1 ethyl (4,5-difluoro-2-nitrobenzoyl)-3-ethoxyacrylate (III, X=fluoro, R=ethyl)

To 3 ml of acetic acid anhydrous were added 3 g (0.01 mol) of ethyl (4,5-difluoro-2-nitrobenzoylacetate and 2.44 g (0.016 mol) of ethylorthoformate.

The reactants were refluxed for about 2 hours.

The reaction product after removing the solvent under reduced prtessure of 10 mmHg was directly used for the next reaction without nay purification.

EXAMPLE 2 ethyl (4,5-difluoro-2-nitrobenzoyl)-3-cyclopropylaminoacrylate (I, X=fluoro, R=ethyl)

A solution of 0.65 g (0.012 mol) of cyclopropylamine was added dropwisely to the compound of the formula (III), wherein X is fluoro and R is ethyl, at 0° C. prepared in Example 1.

After stirring the reactants at 20°±2° C. for 15 min, 2.95 g (yield 87%, wt %), of solid product could be obtained after filtration and drying process.

mp: 123°-125° C.

NMR (CDCl$_3$)ppm: 11.0 (1H, s), 8.76 (1H, d), 7.95-8.23 (1H, q), 6.92-7.33 (1H, q), 3.83-4.23 (2H, q), 2m76-3.33 (1H, m), 0.79-1.03 (7H, m)

IR(KBr): 1685, 1620, 1530, 1410, 1350 cm$^{-1}$

CHN analysis for $C_{15}H_{14}F_2N_2O_5$ calculated value: C63.82, H6.78, N8.23., observed value: C63.79, H6.90, N8.14.

EXAMPLE 3 ethyl-(4-chloro-5-fluoro-2-nitrobenzoyl)-3-ethoxyacrylate (III, X=chloro, R=ethyl)

The procedure of example 1 was repeated while varying the starting compound and the product was obtained. The starting compound was ethyl-4-chloro-5-fluoro-2-nitrobenzoyl acetate (II, X=chloro, R=ethyl)

EXAMPLE 4 ethyl-(4-chloro-5-fluoro-2-nitrobenzoyl)-3-cyclopropylamino acrylate (I, X=chloro, R=ethyl)

The procedure of example 2 was repeated while varying the starting compound and the solid products was obtained (yield 71%, wt %).

The starting compound was the compound of the formula III wherein X is chloro and R is ethyl.

NMR(CDCl$_3$)ppm: 8.15-8.60 (2H, m), 7.20 (1H, d), 3.80-4.20 (2H, q), 2.75-3.35 (1H, m), 0.77-1.01 (7H, m)

What is claimed is:

1. A process for the preparation of nitrobenzoyl-3-cyclopropylaminoacrylate of the formula (I) comprising:

a first stage for the synthesis of nitrobenzoyl-3-alkoxyacrylate of the formula (III), which is prepared by reacting nitrobenzoylester compound of the formula (II) with alkylorthoformate in acetic acid anhydrous; and a second stage for the synthesis of nitrobenzoyl-3-cyclopropylaminoacrylate of the formula (I), which is prepared by reacting nitrobenzoyl-3-alkoxyacrylate of the formula (III) with cyclopropylamine,

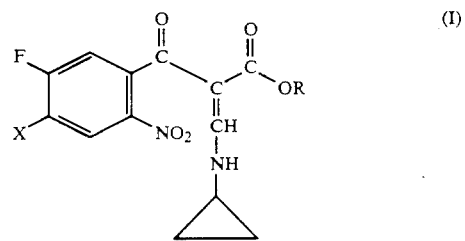

wherein R is methyl, ethyl or propyl and x is chloro, fluoro or bromo,

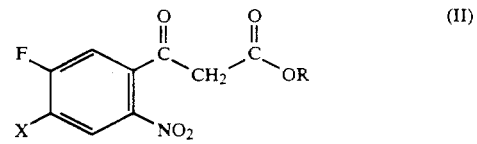

wherein R is methyl, ethyl or propyl and x is chloro, fluoro or bromo,

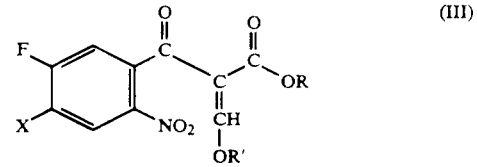

wherein R is methyl, ethyl or propyl and x is chloro, fluoro or bromo and R' is ethyl.

2. The process of claim 1, wherein the first stage reactant is methylorthoformate or ethylorthoformate.

3. The process of claim 1, wherein the first stage reflux time is about 1 to about 5 hours.

4. The process of claim 1, wherein the second stage reaction temperature is about 18° to 30° C. and reaction time is within 1 hour.